United States Patent [19]

Kaminski et al.

[11] 4,423,069

[45] Dec. 27, 1983

[54] CONTRACEPTIVE METHOD

[75] Inventors: Joanne M. Kaminski, Chicago; Ludwig Bauer, Wilmette; Lourens Zaneveld, Forest Park, all of Ill.

[73] Assignee: University of Illinois Foundation, Urbana, Ill.

[21] Appl. No.: 340,975

[22] Filed: Jan. 20, 1982

[51] Int. Cl.³ ............... A61K 31/155; A61K 31/245
[52] U.S. Cl. .................................. 424/310; 560/34; 424/304; 424/251; 424/267; 424/263; 424/270; 424/272; 424/278; 424/285; 546/173
[58] Field of Search ................. 560/34; 424/310, 309

[56] References Cited

U.S. PATENT DOCUMENTS 4,224,342 9/1980 Fujii et al. ........................... 424/310
4,283,418 8/1981 Fujii et al. ........................... 424/310

FOREIGN PATENT DOCUMENTS 1905813 3/1970 Fed. Rep. of Germany ........ 560/34
49-11842 1/1974 Japan ................................... 560/34

*Primary Examiner*—Bernard Helfin
*Attorney, Agent, or Firm*—Merriam, Marshall & Bicknell

[57] ABSTRACT

Contraceptive method comprises maintaining in the genital tract of a mammal an ester of 4-guanidinobenzoic acid and certain substituted phenols in a concentration effective to inhibit the fertilization of ova. In addition to effectively inhibiting the enzymes necessary for conception, the compounds used in the method of the invention are advantageous in possessing low toxicity. Further, the phenolic materials which may be liberated on hydrolysis of the 4-guanidinobenzoates in the genital tract of the animal are low in toxic, caustic or irritating properties, so that the contraceptive compositions are suitable for long-term use without adverse side-effects.

4 Claims, No Drawings

CONTRACEPTIVE METHOD

The U.S. government has rights in this invention pursuant to Contract No. AID/DSPE-C-0035 awarded by the Agency for International Development.

This invention relates to contraceptive methods and compositions for use in mammals and more particularly to such methods wherein certain aryl 4-guanidinobenzoates are used as vaginal contraceptive agents.

BACKGROUND OF THE INVENTION

The compositions which have found practical use as vaginal contraceptives typically incorporate an active ingredient which is spermicidal in effect. In spite of their high spermicidal activity, however, vaginal contraceptives incorporating these materials are not as effective in preventing conception as would be desirable. In addition, there are some indications that these materials possess undesirable side-effects.

In accordance with the invention, there is provided a method for inhibiting conception in mammals in which the contraceptive effects are achieved, not by immobilizing spermatozoa, as in the case of spermicidal contraceptives heretofore known, but by preventing the fusion of spermatozoa with ova by inhibiting one or more of the sperm enzymes necessary for this process, i.e., by functioning as enzyme inhibitors. It has been found that certain compounds, hereinafter described, function as inhibitors of sperm acrosin and possibly other enzymes and have high contraceptive potency when used vaginally in mammals, in a concentration sufficient to prevent fusion of ova and spermatozoa in the presence of the inhibitor.

BRIEF DESCRIPTION OF THE INVENTION

In accordance with the method of the invention, there is maintained in the genital tract of a mammal an ester of 4-guanidinobenzoic acid and certain substituted phenols in a concentration effective to inhibit the fertilization of ova. The active agent is suitably supplied in the form of a composition including the active agent and a pharmaceutically acceptable base or carrier for facilitating handling, application, and retention. In addition to effectively inhibiting the enzymes necessary for conception, the compounds used in the method of the invention, some of which are novel, are advantageous in possessing low toxicity. Further, the phenolic materials which may be liberated on hydrolysis of the 4-guanidinobenzoates in the genital tract of the animal are low in toxic, caustic or irritating properties, so that the contraceptive compositions are suitable for long-term use without adverse side-effects.

DETAILED DESCRIPTION

The active contraceptive agents used in the invention have the formula

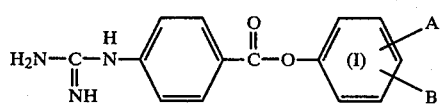

in which A is halo, trihalomethyl, cyano, formyl, R, —OR,

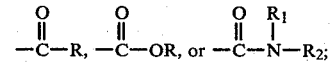

and B is hydrogen or A; wherein R is a lower alkyl group having up to 8 carbon atoms, and $R_1$ and $R_2$ are hydrogen or a lower alkyl group having up to 8 carbon atoms; further provided that A and B together with 2 ring carbon atoms of ring I can form a fused saturated or unsaturated 5- or 6-membered heterocyclic ring containing one or two heteroatoms selected from oxygen, sulfur and nitrogen.

In general, the active contraceptive agents are esters of 4-guanidinobenzoic acid and a mono- or di-substituted phenolic compound. Individual substituents A and B can be located at any of positions 2'–6' in the aromatic ring (ring I) attached to the oxygen atom of the ester. Substituent A can be a halogen atom, i.e., iodine, bromine, chlorine, or fluorine; a trihalomethyl group, such as trifluoromethyl; a cyano (—CN) group; a formyl group; a lower ($C_1$–$C_8$) straight or branched chain alkyl group (R), such as methyl, ethyl isopropyl, n-butyl, sec-butyl, isobutyl, hexyl and iso-octyl; ($C_1$–$C_8$) alkoxy (—OR) such as methoxy; carboalkoxy (—$CO_2R$), such as carbomethoxy; or carboxamido (—$CONH_2$) optionally substituted by one or two lower alkyl groups. Substituent B can be hydrogen or any of the substituents defined as suitable for substituent A. In addition, and when they are attached respectively to adjacent carbon atoms in the O-aryl ring of the compounds (e.g., at vicinal positions 2'–3', or 3'–4'), substituents A and B together can represent a 5- or 6-membered, saturated or unsaturated, heterocyclic ring fused to ring I. Examples of such fused heterocyclic rings are furan, pyrrole, thiophene, tetrahydrofuran, pyrrolidine, piperidine, thiapyran, pyran, pyridine, pyrimidine, thiazole, oxazole, imidazole, and pyrazole.

The aryl guanidinobenzoates useful in the invention can be prepared by the dicyclohexylcarbodiimide (DCC) assisted condensation of 4-guanidinobenzoic acid hydrohalide and an appropriate phenol, in the presence of added 4-toluene sulfonic acid as catalyst in a suitable dry solvent such as pyridine or dimethylformamide, in accordance with the following reaction

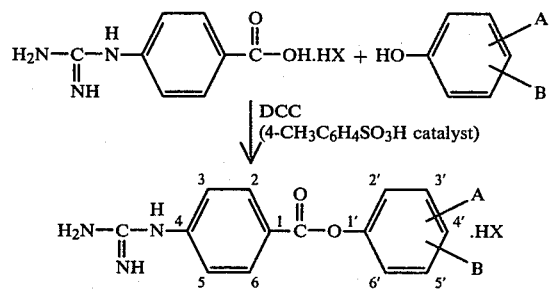

wherein A and B have the meaning previously assigned and X is a halogen atom.

The reaction, which proceeds at room temperature, results in the production of the desired aryl guanidinobenzoate and N,N'-dicyclohexyl urea as a major by-product, from which the desired product can be separated by conventional techniques such as filtration, or extraction with suitable solvents. Depending on the reaction conditions, the desired product can be isolated as the free base or as an inorganic, e.g., hydrochloride, or organic, e.g., citrate or 4-toluene sulfonate, salt thereof. The free base can be converted to a salt and vice versa as desired by conventional means known to those skilled in the art.

The preparation of aryl 4-guanidinobenzoates useful in the invention is illustrated in the following examples. In each case, the following general procedure was used.

General Procedure

A mixture of 4-guanidinobenzoic acid hydrochloride (2.15 g, 0.01 mole), an appropriate phenolic material (0.04 mole), and anhydrous 4-toluenesulfonic acid (0.172 g, 0.001 mole) was suspended or dissolved in freshly distilled dry pyridine (15 ml) at 0° C. for 15 minutes. The system was protected from external moisture by means of a calcium chloride tube. A solution of dicyclohexylcarbodiimide (DCC) (8.24 g, 0.04 mole) in freshly distilled dry dimethylformamide (DMF) (15 ml) was added and the mixture stirred (magnetic stirrer at room temperature until completion of the reaction, for a period ranging from 21 hours to 1 week. At the start of the reaction, a solid began to precipitate and continued to form during the reaction. At the end of the reaction period, residual DCC was destroyed by stirring the reaction mixture for an additional two hours with 2.2 ml of glacial acetic acid.

The desired product was isolated either as the free guanidine base or as a salt thereof. In either case, it was separated from N,N'-dicyclohexyl urea, which is a major by-product. Purification of each product was followed by proton magnetic resonance spectroscopy ($H^1$ NMR). The pure product was crystallized to constant melting point and analyzed for carbon, hydrogen and nitrogen.

EXAMPLE 1

4'-Acetamidophenyl 4-guanidinobenzoate hydrochloride

Using the general procedure and 4-hydroxyacetanilide (acetaminophen) (6.05 g) as the phenolic material, the desired product was isolated as follows:

The reaction mixture was filtered and the insoluble material washed twice with dichloromethane (50 ml). The filtrate was diluted with ice (100 g) and the pH adjusted to 1 with 5 N HCl. The product (44% yield) crystallized as the hydrochloride and was recrystallized from ethanol-hexane. M.p. 251°–254° C. (dec.).

EXAMPLE 2

4'-Carboethoxyphenyl 4-guanidinobenzoate hydrochloride

The general procedure was employed using ethyl 4-hydroxybenzoate as the phenolic material. The desired product was isolated as follows:

The reaction mixture was filtered and the solid product was washed with dichloromethane (50 ml). The insoluble product was identified by $H^1$ NMR as a mixture of the desired aryl 4-guanidinobenzoate hydrochloride and N, N'-dicyclohexyl urea. The N-N' dicylcohexyl urea was removed by extraction with hot chloroform. The residual guanidinobenzoate hydrochloride (70% yield) was then recrystallized from methanol-ether to constant melting point, 207°–210° C. (dec.).

EXAMPLE 3

4'-Carbomethoxyphenyl 4-guanidinobenzoate hydrochloride

This product was prepared in accordance with the general procedure using methyl 4-hydroxybenzoate as the phenolic material. The product (82% yield) was isolated in accordance with the procedure of Example 1. M.p. 257°–259° C. (dec.).

EXAMPLE 4

2'-Carboxamidophenyl 4-guanidinobenzoate hydrochloride

Salicylamide was treated in accordance with the general procedure. The desired product was isolated as follows:

The reaction mixture was filtered and the precipitate washed with dichloromethane (50 ml). The filtrate was diluted with dichloromethane (100 ml) and ice (100 g) and acidified to pH 1 with 5 N HCl. The liquid phases were then separated and the aqueous acidic solution extracted with dichloromethane (50 ml). A gelatin-like precipitate which formed in the aqueous extraction layer on standing at room temperature for 24 hours was filtered and dried under vacuum over $P_2O_5$ for 48 hours. Extraction of the solid with hot chloroform (2×50 ml) and washing with cold methanol (25 ml) yielded the guanidinobenzoate hydrochloride (58% yield) which was recrystallized from methanol-ether to constant melting point, 237°–239° C. (dec.).

EXAMPLE 5

8'-Quinolyl 4-guanidinobenzoate hydrochloride

Using 8-quinolinol and the general procedure, the desired compound (41% yield) was purified in accordance with the method of Example 1. M.p. 245°–249° C. (dec.).

EXAMPLE 6

2'-Carbomethoxyphenyl 4-guanidinobenzoate

Using methyl salicylate and the general procedure, the desired product was isolated as follows:

The reaction mixture was filtered and the precipitate washed with dichloromethane (50 ml). The filtrate was diluted with ice (100 g) and acidified to pH 1 with 5 N HCl. The filtrate consisted of an aqueous layer and a dichloromethane layer. The dichloromethane layer was separated and the aqueous phase extracted with dichloromethane (50 ml). The dichloromethane extracts were combined and washed with cold 5% NaOH (2×50 ml). A light yellow precipitate which formed at this point was filtered and washed with cold $H_2O$ (25 ml). Extraction of the precipitate with hot chloroform (4×25 ml), to remove adhering impurities, yielded the desired guanidinobenzoate ester (70% yield) as the free base, which was recrystallized from absolute ethanol to constant melting point, >290° C. (dec.).

EXAMPLE 7

2'-Methoxy-4'-allylphenyl 4-guanidinobenzoate

Using eugenol as the phenolic material and the general procedure, the desired product was isolated as follows:

The reaction mixture was filtered and the precipitate washed with DMF (50 ml). The filtrate was diluted with ice (100 g) and made alkaline with 5% NaOH. The oily precipitate solidified on the addition of dichloromethane (100 ml). The precipitate was filtered and washed with cold water (25 ml) and dichloromethane (25 ml). The solid material was recrystallized from absolute ethanol to constant melting point and identified as the desired product (85% yield) by H¹ NMR analysis. M.p. >300° C. (dec.).

EXAMPLE 8

3'-Hydroxy-4'-hexylphenyl 4-guanidinobenzoate

Using hexylresorcinol as the phenolic material and the general procedure, the desired product was isolated as follows:

The reaction mixture was filtered and the precipitate washed with DMF (50 ml). The filtrate was diluted with ice (100 g) and made alkaline with 5% NaOH and layered with dichloromethane (2×100 ml). The aqueous and dichloromethane layers were separated and the dichloromethane solution was washed with cold water (3×100 ml). The solid material, recovered by filtration, was extracted with hot chloroform to remove adhering impurities, then crystallized from acetone, and identified as the desired product (65% yield) by H¹ NMR. M.p. 154° C. (dec.).

EXAMPLE 9

2'-Isopropyl-5'-methylphenyl guanidinobenzoate 4-toluenesulfonate

Using the general procedure, and thymol as the phenolic component and 0.01 mole of 4-toluenesulfonic acid, the desired product was isolated as follows:

The reaction mixture was filtered and the precipitate washed with DMF (50 ml). Addition of water (200 ml) caused a formation of a gummy precipitate which was extracted with chloroform. The remaining solid was identified by H¹ NMR as the desired product (75% yield), which was recrystallized from ethanol-ether to constant melting point, 225°–229° C. (dec.).

Other compounds useful in the invention can be made by analogous methods employing starting materials which will be apparent to those skilled in the art. Included among these are 4'-methylumbelliferone 4-guanidinobenzoate (prepared from methylumbelliferone), 2'-methoxy-4'-formylphenyl 4-guanidinobenzoate (from vanillin) and 2'-carbophenoxyphenyl 4-guanidinobenzoate (from phenyl salicylate). The latter two compounds, as well as those of Examples 4, 5, 6, 7, 8 and 9, are novel.

The contraceptive effectiveness of the compounds used in the invention was demonstrated in several ways. In one series of tests, the ability of the compound to inhibit the fertilization of hamster oocytes by human spermatozoa (Rogers et al., *Fertil. Steril.*, 32:664, 1979; Binor et al., *Fertil. Steril.*, 33:321, 1980) was evaluated. In another series of tests, mouse spermatozoa were treated with the test compounds and the ability of the treated spermatozoa to fertilize mouse oocytes in vitro was determined. In a third series of tests, the compounds were mixed with an appropriate carrier or base and placed in the vaginas of mature female rabbits prior to mating with males of known fertility. After a period of at least 36 hours, the conception rate was determined by sacrificing the animals and determining the number of embryos or fetuses. The compounds showed significant contraceptive ability in one or more of the tests.

For practical use as vaginal contraceptive compositions in accordance with the invention, the active agents are mixed with a pharmaceutically acceptable carrier or base to facilitate application to and retention in the genital tract. For this purpose, it is preferred to use a carrier which is viscous or semi-solid, such as a jelly, cream or foam. Examples of suitable carrier materials, which can be used alone or in admixture with appropriate solvents such as water to produce carriers having the desired properties, include polyethylene glycol, polyvinyl pyrrolidone, sodium carboxymethyl cellulose, acacia and tragacanth. Polyethylene glycol having a molecular weight of about 1,000 is a preferred carrier material. The concentration of contraceptive agent in the compositions of the invention is suitably about 0.01 to 20 percent by weight and preferably 0.1 to 10 percent. The actual amount of the composition which should be used for optimum results depends on the size and species of the mammal, and can be readily determined by those skilled in the art. It has been found that after the composition has been deposited and spread in the genital tract, a concentration of about 0.01 to 0.5 percent by weight of active agent in solution or suspension provides effective contraceptive properties.

The foregoing detailed description has been given for clearness of understanding only and, no unnecessary limitations should be understood therefrom as modifications will be obvious to those skilled in the art.

What is claimed is:

1. A method for inhibiting conception in a mammal which comprises maintaining in the genital tract of said mammal an effective amount of a compound having the formula

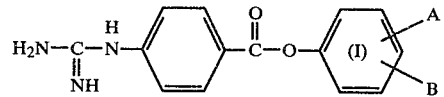

or a pharmaceutically acceptable salt thereof,
in which A is halo, trihalomethyl, cyano, formyl, R, —OR,

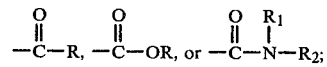

and B is hydrogen or A;
wherein R is a lower alkyl group having up to 8 carbon atoms, and $R_1$ and $R_2$ are hydrogen or a lower alkyl group having up to 8 carbon atoms.

2. The method of claim 1 wherein said compound is selected from the group consisting of
4'-acetamidophenyl 4-guanidinobenzoate
4'-carboethoxyphenyl 4-guanidinobenzoate
4'-carbomethoxyphenyl 4-guanidinobenzoate
2'-carboxamidophenyl 4-guanidinobenzoate
2'-carbomethoxyphenyl 4-guanidinobenzoate
2'-methoxy-4'-allylphenyl 4-guanidinobenzoate
3'-hydroxy-4'-hexylphenyl 4-guanidinobenzoate
2'-isopropyl-5'-methylphenyl 4-guanidinobenzoate.

3. The method of claim 1 wherein said compound is 4'-carboethoxyphenyl 4-guanidinobenzoate.

4. The method of claim 1 wherein said compound is present in solution or suspension in a pharmaceutically acceptable carrier, in a concentration of about 0.01 to 20% by weight.

* * * * *